United States Patent
Brasola et al.

(10) Patent No.: US 10,040,793 B2
(45) Date of Patent: Aug. 7, 2018

(54) KEY INTERMEDIATES AND IMPURITIES OF THE SYNTHESIS OF APIXABAN: APIXABAN GLYCOL ESTERS

(71) Applicant: F.I.S.—FABBRICA ITALIANA SINTETICI S.P.A., Montecchio Maggiore (IT)

(72) Inventors: Elena Brasola, Saccolongo (IT); Filippo Tomasi, Brogliano (IT)

(73) Assignee: F.I.S. FABBRICA ITALIANA SINTETICI S.P.A., Montecchio Maggiore (VI) (IT)

( * ) Notice: Subject to any disclaimer, the term of this patent is extended or adjusted under 35 U.S.C. 154(b) by 0 days.

(21) Appl. No.: 15/827,712

(22) Filed: Nov. 30, 2017

(65) Prior Publication Data

US 2018/0086759 A1    Mar. 29, 2018

Related U.S. Application Data

(62) Division of application No. 15/038,936, filed as application No. PCT/EP2015/053350 on Feb. 18, 2015, now Pat. No. 9,920,051.

(30) Foreign Application Priority Data

Oct. 15, 2014 (EP) .................... 14189007

(51) Int. Cl.
| | | |
|---|---|---|
| *C07D 401/14* | (2006.01) | |
| *C07D 471/04* | (2006.01) | |
| *G01N 30/86* | (2006.01) | |
| *G01N 30/02* | (2006.01) | |

(52) U.S. Cl.
CPC ....... *C07D 471/04* (2013.01); *G01N 30/8631* (2013.01); *G01N 2030/027* (2013.01)

(58) Field of Classification Search
CPC .................................................. C07D 401/14
USPC ........................................................ 546/119
See application file for complete search history.

(56) References Cited

U.S. PATENT DOCUMENTS 7,153,960 B2 * 12/2006 Zhou .................... C07D 211/86
                                                                544/127
2005/0027120 A1   2/2005 Gojon-Zorrilla

FOREIGN PATENT DOCUMENTS

WO    2007001385 A2   1/2007
WO    2013119328 A1   8/2013

OTHER PUBLICATIONS

Pinto et al., "Discovery of 1-(4-Methoxyphenyl)-7-oxo-6-(4-(2-oxopiperidin-1-yl)phenyl)-4,5,6,7-tetrahydro-1H-pyrazolo[3,4-c]pyridine-3-carboxamide (Apixaban, BMS-562247), a Highly Potent, Selective, Efficacious, and Orally Bioavailable Inhibitor of Blood Coagulation Factor Xa", J. Med. Chem., 2007, vol. 50, No. 22, pp. 5339-5356.
International Search Report and Written Opinion for International Application No. PCT/EP2015/053350 (dated Mar. 24, 2015) (9 Pages).

* cited by examiner

*Primary Examiner* — Niloofar Rahmani
(74) *Attorney, Agent, or Firm* — Lucas & Mercanti, LLP

(57) ABSTRACT

Object of the present invention is an improved process for the preparation of Apixaban, through new intermediates which undergo to a faster amidation reaction. Impurities of Apixaban are also identified and quantified.

3 Claims, 1 Drawing Sheet

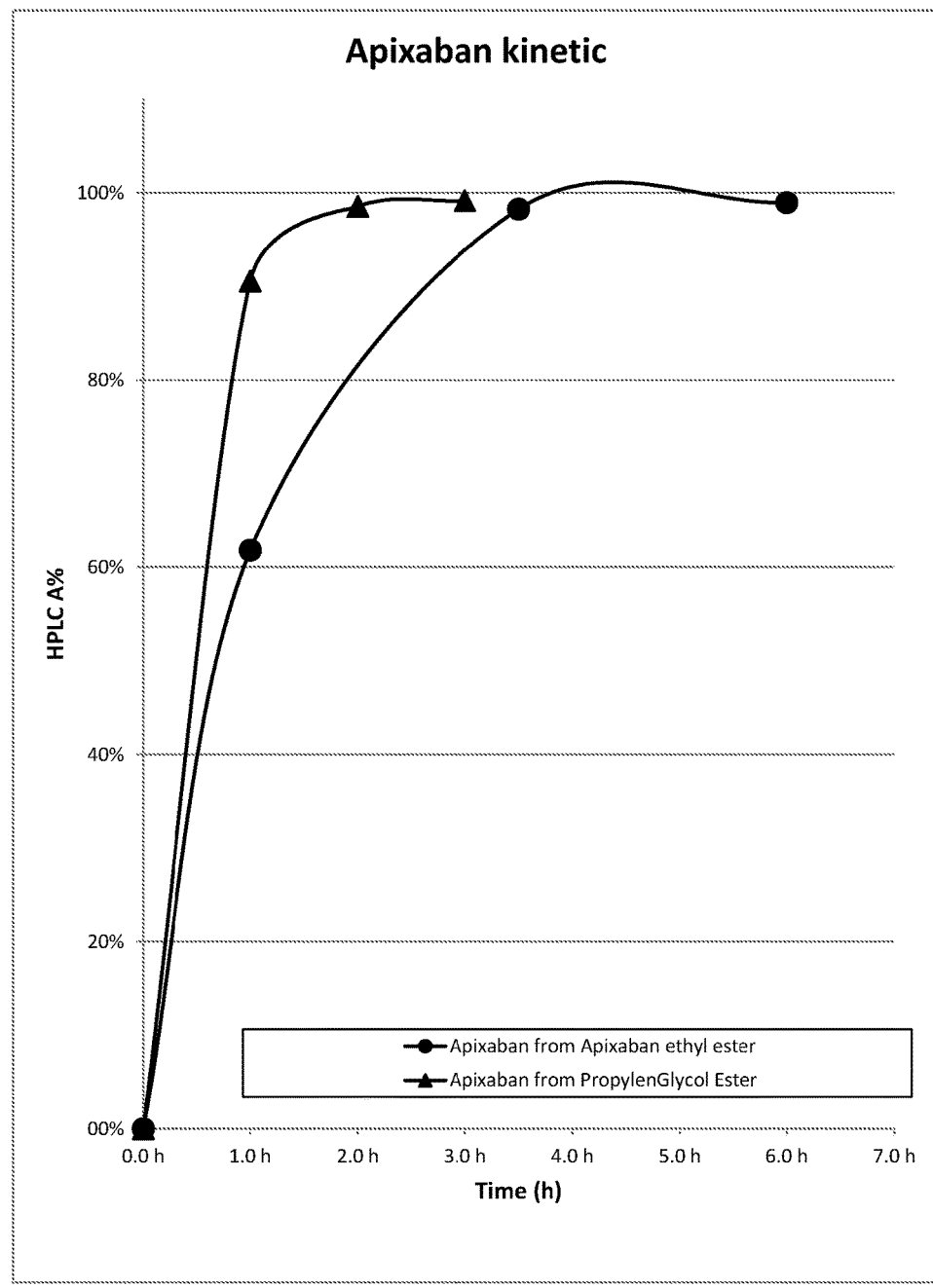

KEY INTERMEDIATES AND IMPURITIES OF THE SYNTHESIS OF APIXABAN: APIXABAN GLYCOL ESTERS

CROSS REFERENCE TO RELATED APPLICATIONS

This application is a Divisional of U.S. application Ser. No. 15/038,936, filed on May 24, 2016, which in turn is a 371 of PCT/EP2015/053350 filed Feb. 18, 2015, which claims the benefit of European Patent Application No. 14189007.9, filed Oct. 15, 2014; the contents of each of which are incorporated herein by reference.

TECHNICAL FIELD

The present invention refers to a process for the preparation the active pharmaceutical ingredient named Apixaban through new key intermediates.

BACKGROUND ART

Apixaban is an active pharmaceutical ingredient used as anticoagulant for the treatment of venous thromboembolic events.

Apixaban has chemical name, 1-(4-methoxyphenyl)-7-oxo-6-[4-(2-oxopiperidin-1-yl)phenyl]-4,5-dihydropyrazolo[5,4-c]pyridine-3-carboxamide and has the following chemical formula (I):

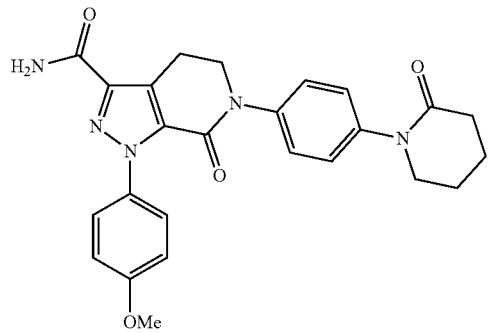

(I)

Some solvates of Apixaban are known, for example, are known the solvates of Apixaban with formamide or with dimethylformamide, both having stoichiometry 1:1.

Apixaban dihydrate, i.e. the hydrate form of Apixaban having two molecules of water per one of Apixaban is also known.

In literature are disclosed some routes of synthesis of Apixaban, in particular, in WO2007/0001385 is described in detail the first industrial synthesis of Apixaban on multi-Kilos scale.

The PCT application WO2007/0001385 discloses in example 6 a process for the preparation of Apixaban by amidation reaction on 10 Kg scale of the Apixaban ethyl ester according to the following reaction scheme:

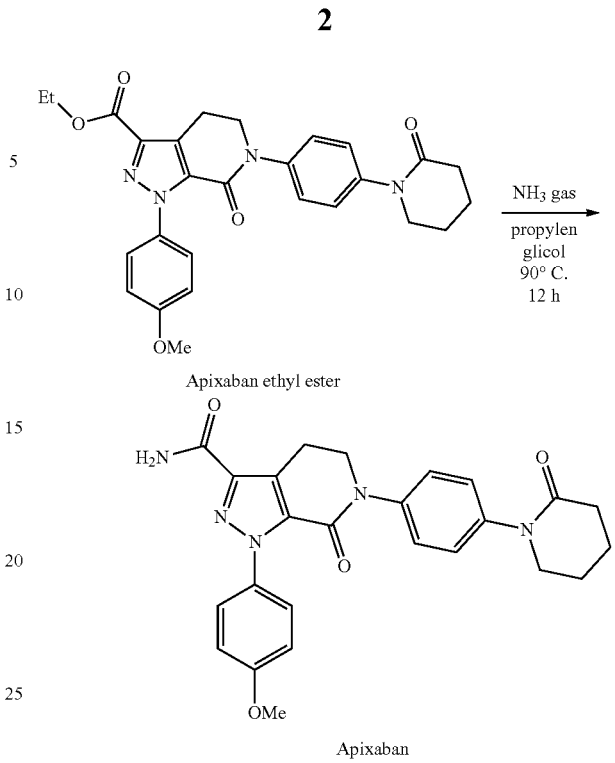

According said procedure, using anhydrous ammonia in propylene glycol and performing the reaction for at least 12 hours at 90° C., Apixaban was obtained with 94.6% of isolated molar yield.

The biggest advantage of the method disclosed in example 6, also in comparison with examples 7 and 9 of WO2007/0001385, is that such a method provides Apixaban having the polymorphic form named N-1, a solid form which is well characterized in example 9 of the same application and which is the thermodynamically stable form of Apixaban.

According to the regulatory information provided by the originator, Apixaban form N-1 is the form currently on the market, so that, with the aim of providing an active pharmaceutical ingredients which provides exactly the same physical-chemical and therapeutical properties of that the originator for the generic market, it is important to find a method for the preparation of Apixaban which provides the polymorphic form N-1.

In the publication J. Med. Chem., 2007, vol. 50, 22, pag. 5339-5356, Apixaban is prepared from Apixaban ethyl ester with aqueous ammonia at 5% in ethylene glycol heating to 120° C. for 4 hours with a molar yield of 76%, according to the following reaction scheme:

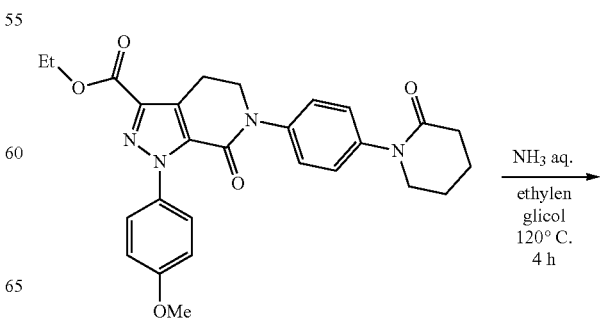

-continued

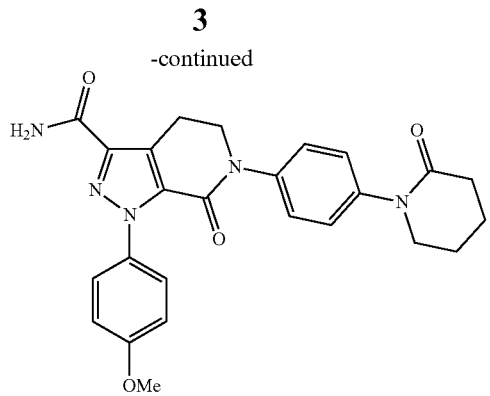

Unfortunately, nothing is said relating to the solid form of Apixaban thus prepared.

The publication Synthetic Communication, 43, pag. 72-79, (2013) discloses a method for the preparation of Apixaban from the intermediate Apixaban ethyl ester using 25% aqueous ammonia in methanol at 65° C. for 5 hours with 91% molar yield.

Nevertheless such a method, probably because is carried out in Methanol instead of in a glycol solvent, does not provide Apixaban form N-1, indeed the m.p. of the product is 171-173° C. which is different from that of the form N-1 being 235-237° C. Moreover no data relating to the purity of the product are provided.

In the patent publication WO2013/119328, example 2, the synthesis of Apixaban was carried out from Apixaban ethyl ester using 5% aqueous ammonia in propylene glycol at 100° C. overnight. The reaction mixture was not seeded with the form N-1 so that at the end of the work-up a different solid form, named Form I, has been isolated. Apixaban Form I thus prepared is Apixaban 1,2-propylen glycol hemisolvate.

Considering the above prior art, and our preliminary experimental results, the presence of a glycol solvent, such as in example 6 of WO2007/0001385, seems to promote the preparation of the polymorphic form N-1, while it appears that the presence of an alcohol solvent as in example 7 and 9 WO2007/0001385 tends to provide the solid form H2-2.

Therefore, to prepare Apixaban form N-1 it appears convenient to isolate Apixaban from a glycol solvent.

Nevertheless, although the industrial method for the preparation of Apixaban form N-1 disclosed in WO2007/0001385 already uses a glycol solvent, such a method has the drawback that it requires long reaction times at high temperature, i.e. at least 12 hours at 90° C. or, according to WO2013/119328, 100° C. overnight, or 4 hours at 120° C. (see above J. Med. Chem. (2007)).

DESCRIPTION OF THE FIGURES

FIG. 1 shows the kinetic study of the conversion of Apixaban glycol ester to Apixaban in comparison to the conversion of Apixaban ethyl ester to Apixaban, both conversion carried out under the same amidation conditions.

SUMMARY OF INVENTION

The problem addressed by the present invention is therefore that of providing an improved process for the preparation of Apixaban and solvates or hydrates thereof which avoids long reaction times and/or high temperatures.

This problem is solved by a process for the preparation of a Apixaban and salts thereof as outlined in the annexed claims, whose definitions are integral part of the present description.

Further features and advantages of the process according to the invention will result from the description hereafter reported of examples of realization of the invention, provided as an indication and not as a limitation of the invention.

DESCRIPTION OF EMBODIMENTS

Object of the present invention is a process for the preparation of Apixaban of formula (I) and solvates or hydrates thereof:

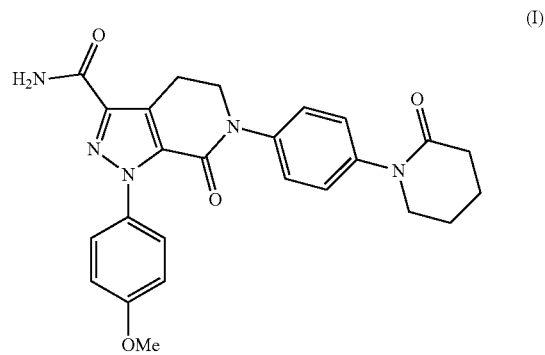 [SMILES: COc1ccc(-n2nc(C(N)=O)c3c2C(=O)N(c2ccc(N4CCCCC4=O)cc2)CC3)cc1]

by amidation reaction of the compound of formula (II):

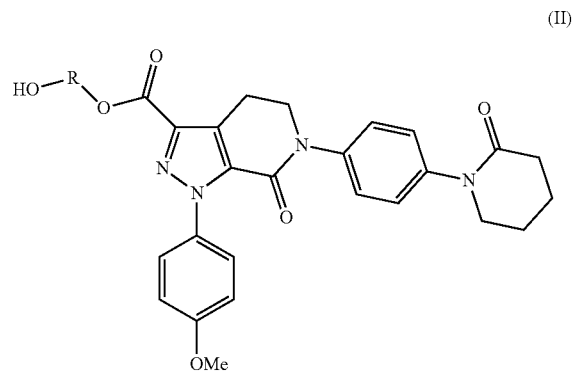

wherein R is chosen from the group comprising a linear or branched $C_2$-$C_6$ alkyl, —$CH_2$—CH(OH)—$CH_2$— and —($R^1$O)$_n$$R^1$— wherein $R^1$ is a linear or branched $C_2$-$C_4$ alkyl and n is an integer from 1 to 6.

It has been indeed surprisingly found that starting from the compound of formula (II), i.e. from a glycol ester for Apixaban, the amidation reaction to convert it to Apixaban proceed much more faster than using the conventional Apixaban C1-C2 alkyl esters.

The effect provided by the compound of formula (II) of the present invention is maybe due to the free oxydryl group that in any way favourites the substitution of the alkoxy group operated by the ammonia, maybe providing a sort of anchimeric assistance. Alternatively, such effect is maybe due to the presence of another oxygen whose electronegativity provide an ester which is easily substituted by the ammonia.

In other words, the glycol esters of Apixaban of formula (II) are converted to Apixaban by means of an amidation reaction much more easily or quickly than the conventional Apixaban esters.

Clear evidences of the effect provided by the process of the invention are provided in the comparative Table 1 and FIG. 1.

Although in some of the following examples the amidation reactions are carried out for 6 hours (just to accomplish to an experimental standard protocol), they were completed well before.

Indeed the amidation reaction of the compound of formula (II) to provide Apixaban lasts typically only 3 hours at a temperature comprised between 80° C. and 90° C., achieving 99.0% of conversion.

As shown in Table I, under exactly the same conditions the conversion of Apixaban ethyl ester to Apixaban takes at least 6 hours.

According to the industrial process disclosed in WO2007/0001385, said conversion lasts at least 12 hours at 90° C.

By comparison with the known amidation reaction of Apixaban esters, the process of the present invention thus requires shorter reaction times.

As a further advantage of the method of the present invention is that the by-product of reaction is a glycol, which can be the solvent medium of the reaction, thus avoiding the presence of further residual solvents and avoiding the presence of alcohol, e.g. ethanol, as by-product that, according to example 7 and 9 of WO2007/0001385, seems to promote the solid form H2-2.

The amidation reaction can be performed using anhydrous ammonia, aqueous ammonia, ammonium salts such as, for example, ammonium hydroxide, ammonium chloride, ammonium bromide, ammonium sulphate, etc.

The amidation reaction of the process of the present invention can be carried out in an aqueous medium and/or in an organic solvent.

The organic solvent can be an alcohol, glycol, ether, ester, nitrile, hydrocarbon, chlorinated hydrocarbon, etc. and mixtures thereof.

The organic solvent can be an alcohol such as for example, methanol, ethanol, isopropanol, butanol, etc.

The organic solvent can be an ether such as methyl-t-buthyl ether, an ester such as ethylacetate or isopropylacetate, a nitrile such as acetonitrile, an hydrocarbon such a toluene or xylene, a chlorinated hydrocarbon such as chloroform, dichloromethane, chlorobenzene, etc.

The glycol solvents are preferred because they provides Apixaban in the solid form N–1 and because, using a glycol solvent of formula HO—R—OH wherein R is the same of that of the compound of formula (II), the by-product of the reaction is the same compound of the solvent, thus avoiding an additional residual solvent to be monitored.

The organic solvent can be an a glycol chosen among ethylenglicol, 1,2-propilenglycol, 1,3-propilenglycol, diethylenglycol, PEG200, Polypropylenglycol, glycerol.

According to a preferred embodiment of the process of the present invention, the preferred solvents are ethylenglicol, 1,2-propylenglycol, 1,3-propylenglycol, diethylenglycol.

The glycol solvent of formula HO—R—OH used in the process of the invention can have the R group with the same meaning of the R group of the compound of formula (II), or, alternatively, R can have a different meaning. According to a referred embodiment, the glycol solvent of formula HO—R—OH has a R group with the same meaning of the R group of the compound of formula (II).

In the compound of formula (II), the R group is chosen from the group comprising a linear or branched $C_2$-$C_6$ alkyl, —$CH_2$—$CH(OH)$—$CH_2$—, —$(R^1O)_n R^1$— wherein $R^1$ is a linear or branched $C_2$-$C_4$ alkyl an n is an integer from 1 to 6.

The linear or branched $C_2$-$C_6$ alkyl is a group chosen in the group comprising $CH_2CH_2$—, —$CH_2CH_2CH_2$—, —$CH_2(CH_3)$—$CH_2$—, —$(CH_2)_4$—, —$CH(CH_3)CH_2CH_2$—, —$CH_2CH(CH_3)CH_2$—, —$CH_2CH_2CH(CH_3)$—, —$(CH_2)_5$—, —$(CH_2)_6$—, etc.

The group —$(R^1O)_n R^1$—, wherein n is an integer from 1 to 6 and wherein $R^1$ is a linear or branched $C_2$-$C_4$ alkyl, is a group chosen in the group comprising —$(CH_2CH_2O)_n CH_2CH_2$—, —$(CH_2CH_2CH_2O)_n CH_2CH_2CH_2$—, —$(CH(CH_3)CH_2O)_n CH(CH_3)CH_2$—, —$(CH_2CH(CH_3)O)_n CH_2CH(CH_3)$—, —$(CH_2CH_2CH_2CH_2O)_n CH_2CH_2CH_2CH_2$—, etc.

According to a preferred embodiment, the group —$(R^1O)_n R^1$— is —$(CH_2CH_2O)_n CH_2CH_2$—.

According to a preferred embodiment of the present invention, the compound of formula (II) is a compound isolated, i.e. a compound isolated from the reaction mixture from which it is prepared. Therefore, the compound of formula (II) is typically in form of a solid or of an isolated oil.

According to a preferred embodiment of the present invention, the compound of formula (II) is a compound having a purity higher than 80%, measured in HPLC A/A%, for example by using the analytical method of example 13.

The process of the present invention is carried out at a temperature comprised between 60° C. and 140° C., preferably between 80° C. and 120° C., more preferable between 80° C. and 90° C.

When the amidation reaction is carried out between 80° C. and 90° C., the reaction is completed (i.e. conversion higher than 99%) in about 3 hours.

According to a preferred embodiment, the process of the present invention further comprises the step of preparation of the compound of formula (II):

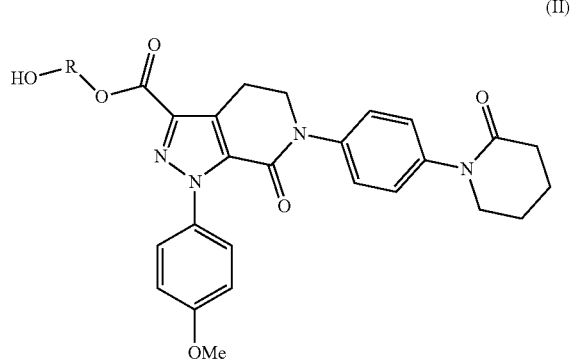

(II)

wherein R is chosen from the group comprising a linear or branched $C_2$-$C_6$ alkyl, —$CH_2$—$CH(OH)$—$CH_2$— and —$(R^1O)_n R^1$— wherein $R^1$ is a linear or branched $C_2$-$C_4$ alkyl and n is an integer from 1 to 6, by means of a transesterification reaction of the compound of formula (III):

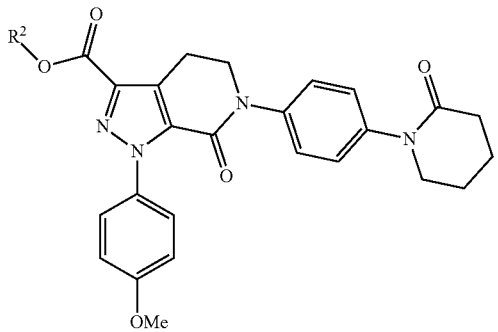

(III)

wherein $R^2$ is a linear or branched $C_1$-$C_6$ alkyl.

The transesterification of the compound of formula (III) to provide the compound of formula (II) is thus carried out by reaction of the compound of formula (III) with a glycol, with a polyglycol or with glycerol.

The transesterification reaction is carried out by reaction of a glycol of formula OH—R—OH where R is chosen from the group comprising a linear or branched $C_2$-$C_6$ alkyl, —$CH_2$—CH(OH)—$CH_2$— and —$(R^1O)_nR^1$— wherein $R^1$ is a linear or branched $C_2$-$C_4$ alkyl and n is an integer from 1 to 6.

Preferred glycols are ethylenglycol, 1,2-propylenglycol, 1,3-propylenglycol and diethylenglycol.

Preferred polyglycols are Polyethylenglycol (200) (abbreviated PEG200) and Propylenglicol 200 (PPG200). PEG has the following chemical structure HO—$(CH_2CH_2O)_n$ $CH_2CH_2$—OH.

The transesterification reaction can be carried out at a pH comprised between 7.5 and 10.0, preferably at pH comprised between 8.0 and 9.5.

The transesterification reaction can be carried out in presence of bases, preferably inorganic bases such as, preferably, $NaHCO_3$ or $KH_2PO_4$, i.e. bibasic potassium phosphate.

The transesterification reaction is preferably carried out in presence of bibasic potassium phosphate since it provides the higher and faster conversions.

The transesterification reaction is carried out at a temperature comprised between 60° C. and 120° C., preferably between 70° C. and 80° C., more preferably at about 75° C.

The transesterification reaction is carried out using an excess of the reactant glycol as reaction solvent.

According to an alternative route of synthesis, the compound of formula (II) can be prepared by inner cyclization of the compound of formula (IV):

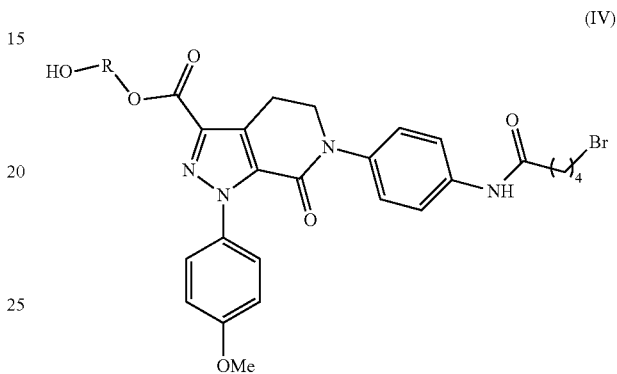

(IV)

wherein R is chosen from the group comprising a linear or branched $C_2$-$C_6$ alkyl, —$CH_2$—CH(OH)—$CH_2$— and —$(R^1O)_nR^1$— wherein $R^1$ is a linear or branched $C_2$-$C_4$ alkyl and n is an integer from 1 to 6.

The compound of formula (IV) can be prepared adapting the known prior art methods used for the preparation of the correspondent esters to the preparation of said Apixaban glycol ester. Using this synthetic approach, the compound of formula (II) can be prepared avoiding the preparation of the previous Apixaban esters of formula (III). See reaction scheme below.

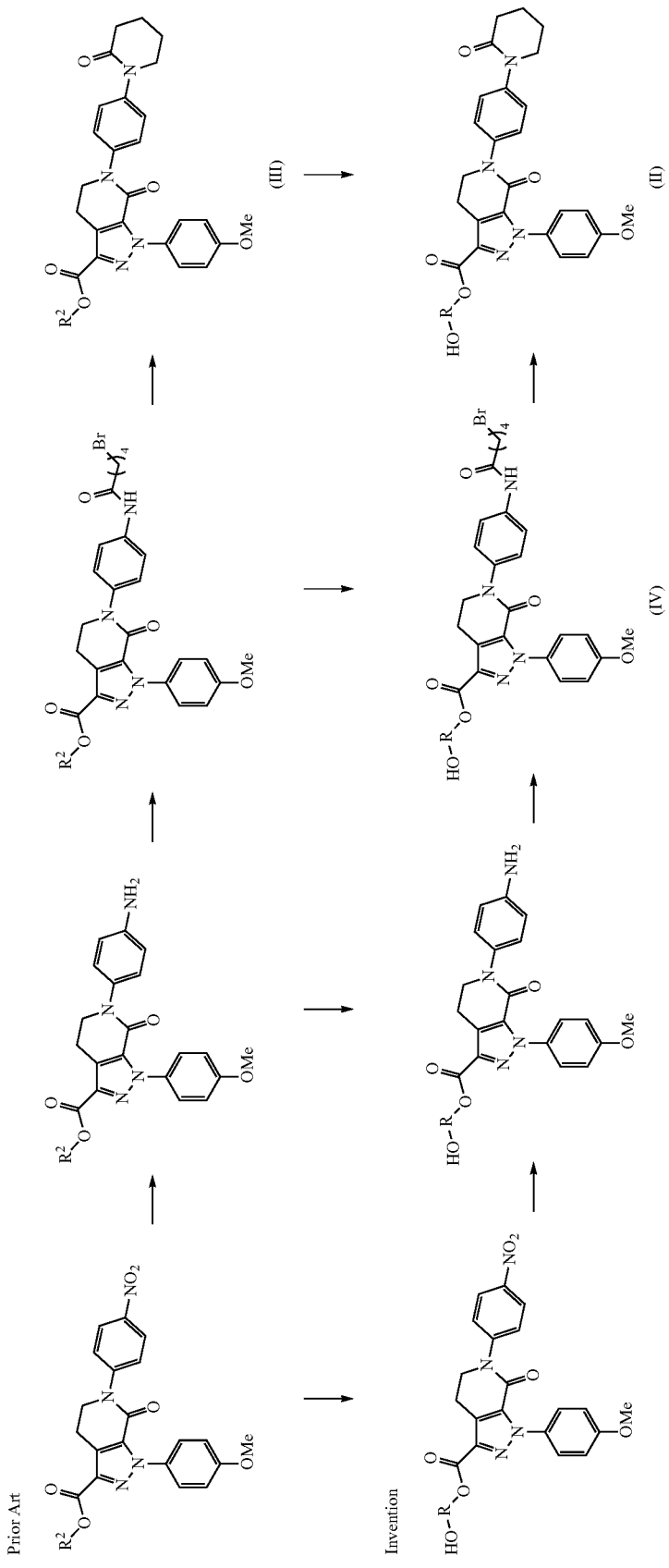

The cyclization of the compound of formula (IV) to provide the compound of formula (II) can be carried out in presence of a base such, for example, t-BuOK.

Moreover, the compound of formula (II) can be prepared according to other synthetic approach which do not necessarily involve the preparation of the compound of formula (III) or, however, esters intermediates.

In the following reaction scheme is described an example of direct synthesis of the compound of formula (II) by reaction of the glycol ester of the hydrazone starting material.

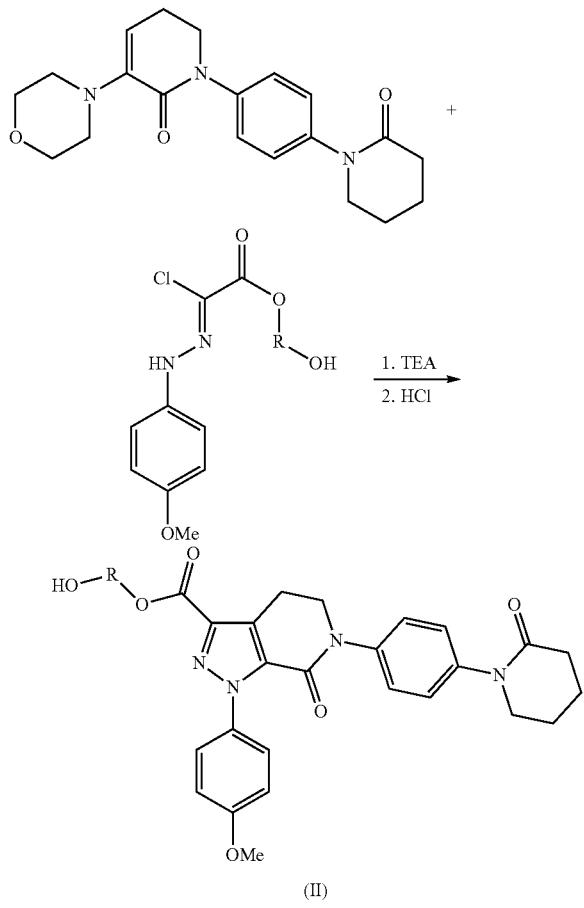

wherein R is chosen from the group comprising a linear or branched $C_2$-$C_6$ alkyl, —CH$_2$—CH(OH)—CH$_2$— and —(R$^1$O)$_n$R$^1$— wherein R$^1$ is a linear or branched $C_2$-$C_4$ alkyl and n is an integer from 1 to 6.

According to a preferred embodiment, in the process of the present invention for the preparation of Apixaban and/or in the further step of preparation of the compound of formula (II) starting from the compound of formula (III), the R group in the compound of formula (II) is chosen from the group comprising —CH$_2$CH$_2$—, —CH$_2$CH(CH$_3$)—, CH(CH$_3$)CH$_2$—, —(CH$_2$)$_3$— and CH$_2$CH$_2$OCH$_2$CH$_2$—, or according to another embodiment, chosen from the group comprising —CH$_2$CH$_2$—, —(CH$_2$)$_3$— and CH$_2$CH$_2$OCH$_2$CH$_2$—.

Said compounds of formula (II) can be conveniently prepared by transesterification of the compound of formula (III), wherein R is for example ethyl, respectively with ethylenglycol, 1,2-propylenglycol, 1,3-propylenglycol and diethylenglycol or, according to another embodiment, respectively with ethylenglycol, 1,3-propylenglycol and diethylenglycol.

The compound of formula (II) prepared from the compound of formula (III) by transesterification with 1,2-propanediol, is a mixture of the two isomers with ratio 1:2 wherein R is —CH(CH$_3$)CH$_2$, named Isomer A, or R is —CH$_2$CH(CH$_3$)—, named Isomer B, i.e. having respectively the following structures:

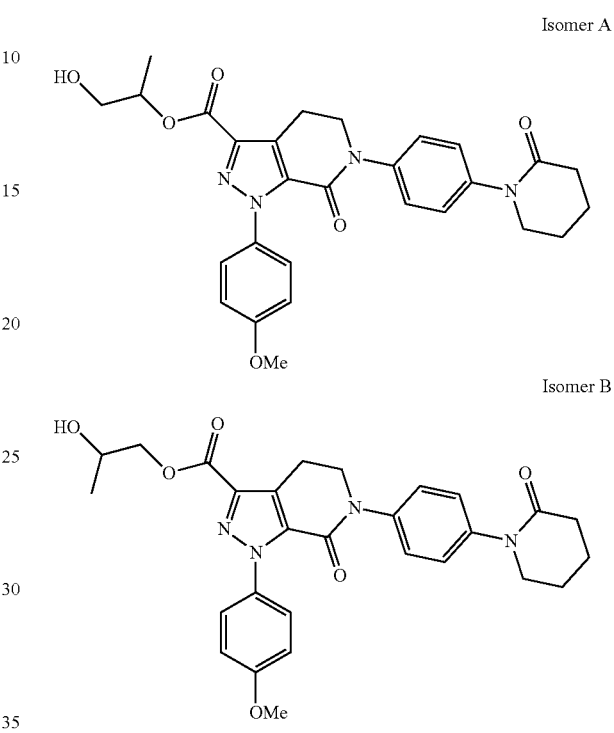

It has been observed that the Isomer A (compound (II) with R=—CH(CH$_3$)CH$_2$—) has RRT=1.18 according to the analytical method described in example 13 while the Isomer B (compound (II) with R=—CH$_2$CH(CH$_3$)—) has RRT=1.16 according to the same analytical method.

The compound of formula (II) wherein R is —CH$_2$CH(CH$_3$)—, i.e. the isomer B, is preferred since this is the main isomer compound prepared by transesterification reaction of the compound of formula (III) with 1,2-propylen glycol.

The compound of formula (II) prepared from the compound of formula (III) by transesterification with ethylenglycol, has instead the only one following structure:

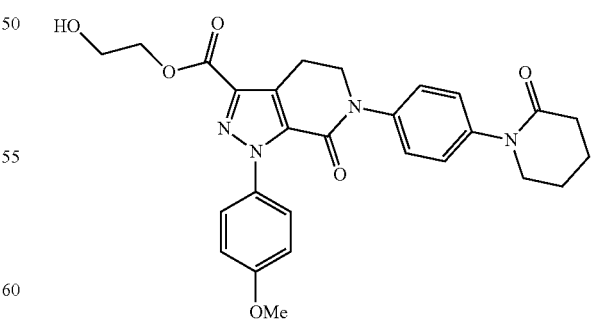

According to a preferred embodiment of the process of the present invention, the R substituent of the compound of formula (II) is chosen from the group comprising —CH$_2$CH$_2$—, —CH$_2$CH(CH$_3$)—, —CH(CH$_3$)CH$_2$—, —(CH$_2$)$_3$—, and —CH$_2$CH$_2$OCH$_2$CH$_2$—.

According to a another preferred embodiment of the of the process of the present invention, the R substituent of the compound of formula (II) is chosen from the group comprising —CH$_2$CH$_2$—, —(CH$_2$)$_3$— and —CH$_2$CH$_2$OCH$_2$CH$_2$—.

Object of the present invention is thus also the compound of formula (II):

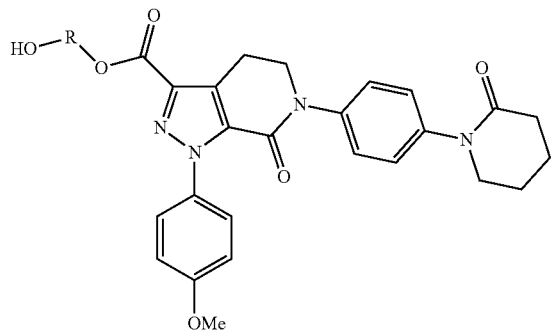

(II)

wherein R is chosen from the group comprising a linear or branched C$_2$-C$_6$ alkyl, —(R$^1$O)$_n$R$^1$— wherein R$^1$ is a linear or branched C$_2$-C$_4$ alkyl an n is an integer from 1 to 6, and the group —CH$_2$—CH(OH)—CH$_2$—.

According to a preferred embodiment of the compound of formula (II) of the present invention, R is chosen from the group comprising —CH$_2$CH$_2$—, —CH$_2$CH(CH$_3$)—, CH(CH$_3$)CH$_2$—, —(CH$_2$)$_3$— and —CH$_2$CH$_2$OCH$_2$CH$_2$—.

According to a another preferred embodiment of the compound of formula (II) of the present invention, R is chosen from the group comprising —CH$_2$CH$_2$—, —(CH$_2$)$_3$— and —CH$_2$CH$_2$OCH$_2$CH$_2$—.

The compound of formula (II) of the present invention can be thus used for the preparation of Apixaban of formula (I) and solvates or hydrates thereof.

According to an embodiment of the present invention, the process for the preparation of Apixaban of formula (I) and solvates or hydrates thereof:

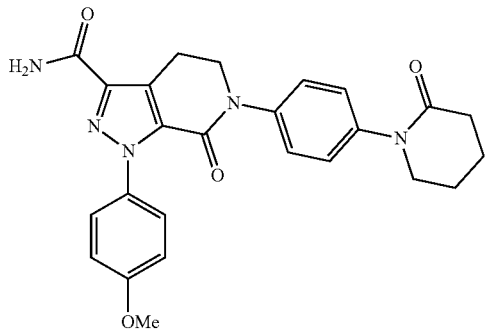

(I)

comprises the following steps:
a) transesterification reaction of the compound of formula (III):

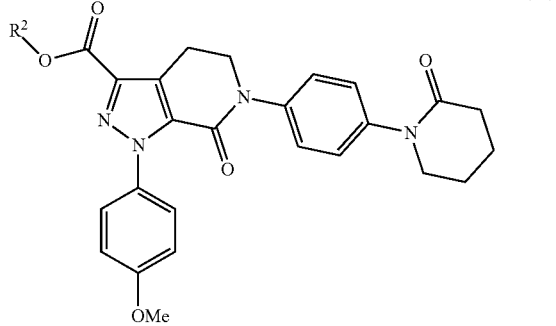

(III)

wherein R$^2$ is a linear or branched C$_1$-C$_6$ alkyl,
to provide the compound of formula (II):

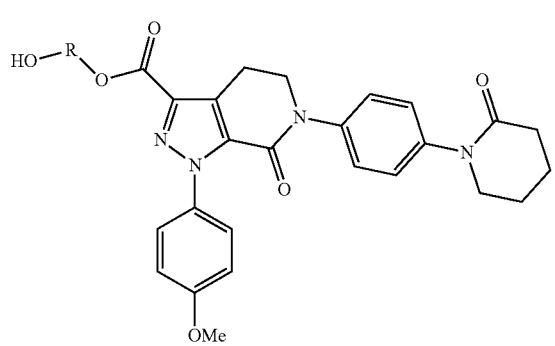

(II)

wherein R is chosen from the group comprising a linear or branched C$_2$-C$_6$ alkyl, —CH$_2$—CH(OH)—CH$_2$— and —(R$^1$O)$_n$R$^1$— wherein R$^1$ is a linear or branched C$_2$-C$_4$ alkyl and n is an integer from 1 to 6,
b) isolating the compound of formula (II),
c) amidation reaction of the compound of formula (II):

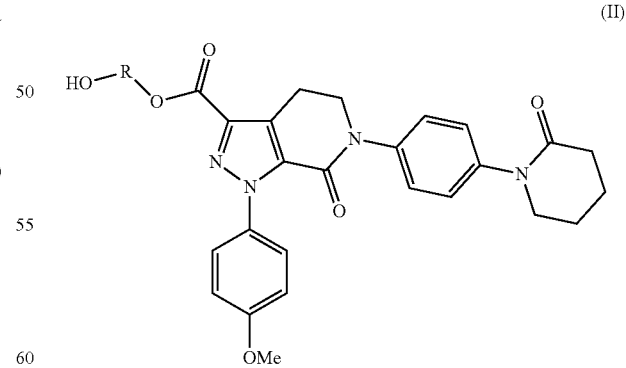

(II)

to provide Apixaban of formula (I).

According to this above embodiment of the process of the present invention, the compound of formula (II) is a useful intermediate for the preparation of Apixaban which allows to insert a further step in the known synthesis of Apixaban by direct amidation reaction of Apixaban esters.

Indeed, starting from Apixaban esters of formula (III) and preparing and isolating of the compound of formula (II), allows to increase the purity of the said intermediate of formula (II), thus increasing the purity of the final Apixaban.

In other words, performing the process of the invention according said preferred embodiment, wherein the intermediate of formula (II) is isolated, by comparison with the known process of direct conversion of Apixaban esters of formula (III) to Apixaban, said process allows the improve the purity of the final product Apixaban.

The isolation of the compound of formula (II) in the step (b) can be carried out by the known techniques of organic synthesis, including precipitation and filtration or centrifugation, or, alternatively, phases separation.

At the end of the step (b) the compound of formula (II) can be optionally dried, in oven or within the filter drier.

Moreover, isolating the compound of formula (II) can be useful to satisfy the requirements of Regulatory authorities, which require the process being composed by at least three synthetic steps.

According to the just mentioned preferred embodiment of the process of the present invention, it is a preferred process that wherein $R^2$ in the compound of formula (III) is ethyl.

According to the just mentioned preferred embodiment of the process of the present invention, it is a preferred process that wherein R in the compound of formula (II) is chosen from the group comprising —$CH_2CH_2$—, —$CH_2CH(CH_3)$—, $CH(CH_3)CH_2$—, —$(CH_2)_3$— and —$CH_2CH_2OCH_2CH_2$—.

According to the just mentioned preferred embodiment of the process of the present invention, it is another preferred process that wherein R in the compound of formula (II) is chosen from the group comprising —$CH_2CH_2$—, —$(CH_2)_3$— and —$CH_2CH_2OCH_2CH_2$—.

According to the just mentioned preferred embodiment of the process of the present invention, it is a preferred process wherein $R^2$ in the compound of formula (III) is ethyl and wherein R in the compound of formula (II) is chosen from the group comprising —$CH_2CH_2$—, —$CH_2CH(CH_3)$—, $CH(CH_3)CH_2$—, —$(CH_2)_3$— and —$CH_2CH_2OCH_2CH_2$—.

According to the just mentioned preferred embodiment of the process of the present invention, it is another preferred process wherein $R^2$ in the compound of formula (III) is ethyl and wherein R in the compound of formula (II) is chosen from the group comprising —$CH_2CH_2$—, —$(CH_2)_3$— and —$CH_2CH_2OCH_2CH_2$—.

The conditions to performs the steps (a) and (c) of the preferred embodiment of the invention just mentioned are the same of that already described above for the process of the invention, including the preferred embodiments thereof.

Just like any compound obtained by means of chemical synthesis, Apixaban, and solvates or hydrates thereof, may contain small amounts of foreign compounds referred to as impurities. These impurities may be the raw materials, synthetic intermediates, reaction by-products, degradation products etc.

The impurities of Apixaban just like those of any other pharmaceutical active ingredient or relative drug, referred to as "pharmaceutical impurities", may affect both the efficiency and the safety of a drug which, in extreme cases, could even be harmful for the patient. The purity of an active ingredient like the Apixaban produced through a production process based on subsequent chemical reactions represents a critical factor as regards commercialization. The US Food and Drug Administration (FDA) and the European Medicinal Agency (EMA) as well as the relative pharmacopoea require that the impurities be maintained below given limit values.

The product of a chemical reaction is rarely a single compound having purity sufficient to meet the regulatory standards. By-products due to secondary reactions of the reagents used in the reaction can also be present in the isolated product. In some steps of the production process of an active ingredient, such as Apixaban, the purity is analysed, generally by means of high performance liquid chromatography (HPLC), gas chromatography (GC) or thin layer chromatography (TLC), for defining if it is suitable for the subsequent treatment and lastly for use in the pharmaceutical product.

Generally, the impurities are identified spectroscopically, thus a chromatographic peak position, such as that of a chromatogram or a spot on a TLC panel, is associated thereto.

Once a peak position has been associated to a particular impurity, the impurity can be identified in a sample for the relative position thereof in the chromatogram, where the position in the chromatogram is measured in minutes between the injection of the sample in a column and elution of the impurity through the detector. The position in the chromatogram is known as the retention time and the ratio between the retention times is known as the relative retention time.

A man skilled in pharmaceutical art knows that a relatively pure compound may be used as a reference standard. A reference standard is similar to a reference marker, except for the fact that the latter can be used not only for detecting the impurities, but also for quantifying the amount of impurities present in the sample of active ingredient.

As known to those skilled in the art, the management of process impurities is considerably improved by understanding the chemical structures thereof, the synthetic process and identifying the parameters that affect the amount of impurities in the final product for example by means of DOE. The impurities of Apixaban, including the intermediaries not entirely reacted, the impurities of the raw materials, the reaction by-products, the degradation products, as well as other products, may affect the quality and efficiency of the pharmaceutical form containing Apixaban. Thus, there arises the need for a method for defining the level of impurities in samples of Apixaban and methods for removing the impurities or limiting the content thereof or preventing the formation thereof.

As one other aspect of the present invention, during the development of the process for the preparation of Apixaban, it has been found that the compound of formula (II) tends to remain into the product Apixaban, in other words, the compound of formula (II) is both a starting material or intermediate for the synthesis of Apixaban according to the method of the present invention and is also an impurity of Apixaban.

In order to reduce the amount of an impurity in an active ingredient it is necessary to detect the presence thereof using appropriate analytical methods, it is convenient to identify it, quantify it and only afterwards one can provide a method of synthesis capable of preventing the formation and/or provide for the removal thereof. However, this essentially requires providing the reference standard or reference marker of this impurity. For such purpose the compound of formula (II) can be conveniently prepared by means of the method described above.

The compound of formula (II) of the present invention can be thus used as reference marker or reference standard for the identification and/or quantification of said compound of formula (II) in Apixaban and solvates or hydrates thereof.

The compound of formula (II) can be indeed used according to the following analytical methods the identification and/or quantification of said compound of formula (II) in Apixaban and solvates or hydrates thereof.

A method for detecting or identifying the compound of formula (II) in Apixaban or a solvate or hydrate thereof comprises:

a) adding a known amount of compound of formula (II) to the Apixaban sample or a solvate or hydrate thereof,
b) carrying out HPLC analysis of the Apixaban sample or a solvate or hydrate thereof of step a),
c) detecting the HPLC peak of the compound of formula (I);
or,
a1) analysing the compound of formula (II) by means of HPLC,
b1) analysing the Apixaban sample or a solvate or hydrate thereof by means of HPLC,
c1) detecting the HPLC peak of the compound of formula (II) by comparing the retention times or relative retention times.

Substantially using the method above, it allowed identifying the peak in the chromatogram of Apixaban sample or a solvate or hydrate thereof regarding the impurity compound of formula (II). The analysis may be of the HPLC type.

Besides the identification of the impurity peak in Apixaban or a solvate or hydrate, a method for the quantification of the compound of formula (II) in Apixaban or a solvate or hydrate thereof comprises:

i) measuring the peak area corresponding to the compound of formula (II) in a Apixaban sample or a solvate or hydrate thereof having an unknown amount of compound of formula (II) by means of HPLC;
ii) measuring the peak area corresponding to a reference standard containing a known amount of compound of formula (II) by means of HPLC;
iii) defining the amount of compound of formula (II) in Apixaban or a solvate or hydrate thereof comparing the area measured in step a) with that measured in step ii).

It is thus clear that the compound of formula (II) may be used as a reference marker or reference standard respectively for the identification and/or the quantification of the same in Apixaban or a solvate or hydrate thereof.

In particular, it has been observed that the impurity of Apixaban produced according to the process of the present invention and having RRT=1.16 with the analytical method reported in example 13 is the Isomer B of the following structures, while the impurity having RRT=1.18 has the is the Isomer A of the following structures:

Isomer A

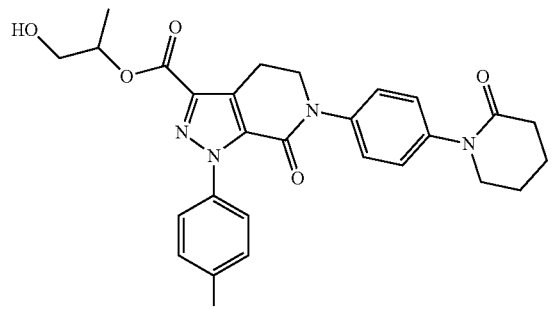

RRT = 1.18

Isomer B

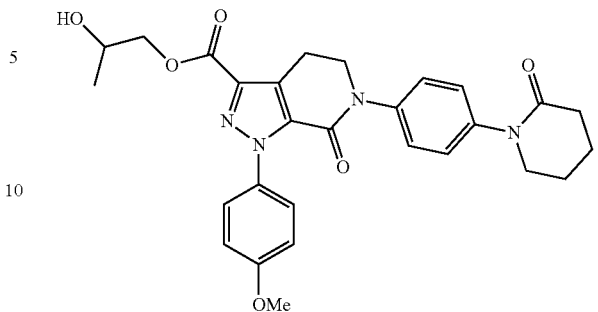

RRT = 1.16

As an aspect related to the solid form of Apixaban produced by the process of the present invention, a study directed to the preparation of Apixaban solid form N-1 was carried out.

Repeating the experiment of example 6 of WO2007/0001385 but without adding the seed of form N-1, it has been obtained, prepared and characterized Apixaban 1,2-Proprylen glycol hemisolvate of formula (V):

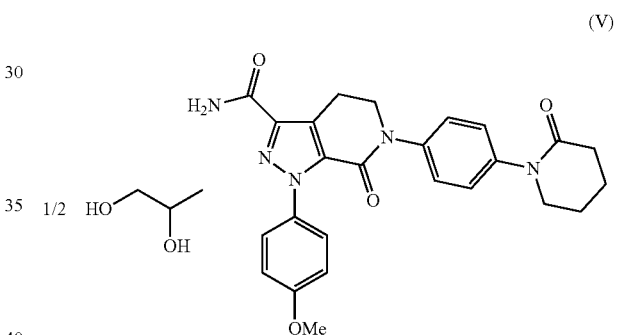

(V)

Apixaban 1,2-propylene glycol solvate having stoichiometry (2:1) of formula (V) is a white solid.

After that, a study directed to find a method to obtain N-1 form from Apixaban 1,2-proprylen glycol hemisolvate of formula (V) was carried out.

A screening using Apixaban 1,2-propylene glycol hemisolvate (abbreviated APX•PG) as starting material was performed using form N-1 as a seed in all the cases. The experiments were performed with ICH guideline class 3 solvents (except MeOH, ICH guideline class 2 with a residual solvent permitted of 3000 ppm). The low solubility of APX•PG with common industrial solvents limited the use of the crystallization.

The successful experiments that provided Apixaban form N-1 from APX•PG are collected in Table 1.

TABLE 1

Methods of preparation of Apixaban form N-1 from APX•PG.

| # | scale | method | solvent | T° | time | Yield |
|---|-------|--------|---------|-----|------|-------|
| 1 | 250 mg | Crystallization | MeOH (36 v.) | Reflux →*rT° | 4 hours | 76% |
| 2 | 250 mg | Crystallization | EtOH (60 v.) | Reflux →*rT° | 4 hours | 83% |

TABLE 1-continued

Methods of preparation of Apixaban form N-1 from APX•PG.

| # | scale | method | solvent | T° | time | Yield |
|---|---|---|---|---|---|---|
| 3 | 100 mg | Slurrying | MeOH (10 v.) | rT° | overnight | 87% |
| 4 | up to 1 g | Slurrying | EtOH (10 v.) | rT° | 4 hours | 86% |
| 5 | up to 1 g | Slurrying | IPA (10 v.) | 50° C. | overnight | 89% |
| 6 | 500 mg | Slurrying | EtOH/ heptane (10 v.) | rT° | 6 hours | 90% |
| 7 | 50 mg | Slurrying | EtOAc (10 v.) | rT° | overnight | 93% |

Slurrying seems to be the best procedure to prepare form N-1 because a high amount of solvent was required in crystallizations (36-60 volumes).

Due to their lower boiling points and the good industry acceptance, EtOH and IPA were selected as solvents to perform a scale-up of the slurrying experiments to 1 g. The transformation was monitored by XRPD:

In EtOH the transformation was finished after 1 hour at room temperature.

In IPA the transformation is much slower: after 5 h at 50° C., the conversion was not complete, but finished after one night.

Propylene glycol was not detected in Apixaban form N-1 by $^1$H-NMR. Unfortunately, residual solvent was detected by $^1$H-NMR in both experiments (approx. 0.8 wt % of EtOH and 0.7 wt % of IPA). The NMR analysis indicated also 0.7 wt % of residual solvent when EtOAc was used.

$^1$H-NMR analyses of form N-1 obtained in EtOH by crystallization and slurrying indicated that the amount of residual solvent is lower in the case of the crystallization (0.4 wt % instead of 0.8 wt %). The method of preparation seems to have some effect on the final amount of residual solvent (perhaps due to the different particle sizes or kind of aggregates).

Typically, the Apixaban form N-1 prepared according to the process of the invention has a water content comprised between 0.05% and 0.1%.

EXPERIMENTAL SECTION

The starting material Apixaban ethyl ester can be prepared according to Example 5 of WO2007/001385.

Example 1

Preparation of Apixaban 1,2-propylen glycol hemisolvate of formula (V) from Apixaban ethyl ester.

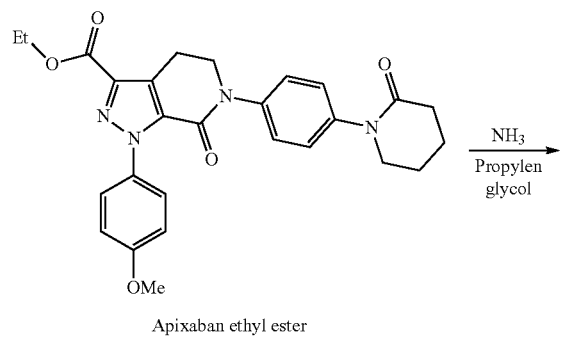

Apixaban ethyl ester

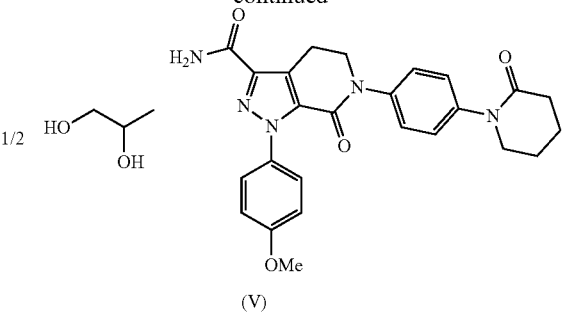

(V)

In an autoclave inerted by nitrogen Apixaban ethyl ester (15 g, 1.0 eq) and propylene glycol (1,2-propan diol, 135 mL) were charged and the vessel was pressurized with ammonia at p=4 bar and T=80/85° C. for 6 h. The mixture was then transferred in a round bottom flask, cooled to 45/50° C. and diluted with water (85 mL). After stirring at T=45/50° C. for additional 2 h, the suspension was cooled to 20/25° C. for 10 h and filtered. The wet cake was washed with water (2×30 mL). The solid was dried under vacuum at T=75° C. for 8 h affording Apixaban 1,2-propylenglycol hemisolvate of formula (V) (13.3 g, 0.86 eq). m.p. 195° C. $^1$H-NMR (400 MHz, CDCl$_3$, ppm), δ: 7.49 (d, J=9 Hz, 2H), 7.35 (d, J=8 Hz, 2H), 7.28 (d, J=8 Hz, 2H), 6.95 (d, J=9 Hz, 2H), 6.91 (s, 1H), 5.91 (s, 1H), 4.13 (t, J=8 Hz, 2H), 3.84 (bs, 3H+0.5H CH propylene glycol), 3.62 (bm, 2H+0.5H OH propylen glycol), 3.39 (bm, J=8 Hz, 2H+0.5H OH propylen glycol), 2.57 (bs, 2H+1H CH$_2$ propylen glycol), 1.95 (bs, 4H), 1.14 (d, J=6.4 Hz, 1.5H CH$_3$ propylen glycol). 13C NMR and DEPT 135 NMR (100 MHz, CDCl$_3$, ppm), δ: 170.3 (C), 163.8 (C), 159.9 (C), 157.4 (C), 141.4 (C), 140.7 (C), 140.0 (C), 133.4 (C), 132.5 (C), 126.8 (CH), 126.2 (CH), 126.5 (CH), 125.9 (CH), 113.8 (CH), 68.3 (CH), 68.1 (CH$_2$), 55.6 (CH$_3$), 51.6 (CH$_2$), 51.2 (CH$_2$), 32.8 (CH$_2$), 23.5 (CH$_2$), 21.4 (CH$_2$), 21.3 (CH$_2$), 18.8 (CH$_3$). ESI-MS m/z=460 ([M+H]$^+$). IR (ATR, cm$^{-1}$): 3447, 3145, 2940, 2860, 1687, 1631, 1543, 1512, 1465, 1441, 1401, 1380, 1350, 1326, 1297, 1243, 1170, 1144, 1111, 1027, 1016, 982, 945, 831, 812, 761, 705. X-RPD)(2θ°): 6.6°, 7.6°, 8.1°, 9.9°, 11.7°, 12.7°, 13.7°, 14.5°, 15.1°, 15.6°, 16.3°, 16.9°, 17.2°, 17.9°, 18.2°, 19.5°, 20.0°, 20.5°, 20.8°, 21.4°, 22.8°, 23.8°, 24.8°, 25.5°, 29.0°, 31.2°, 33.0°.

The reworking of example 6 of WO2007/001385, carried out many times but without adding the seeds of Apixaban form N-1, always provided Apixaban 1,2-propylen glycol hemisolvate of formula (V).

le;3qThis is in agreement with the teachings of the patent publication WO2013/119328 wherein Apixaban form I, i.e. Apixaban 1,2-propylen glycol hemisolvate was obtained without the seeding with form N-1.

Example 2

Preparation of Apixaban form N-1 from Apixaban 1,2-propylen glycol hemisolvate—without seeding of form N-1.

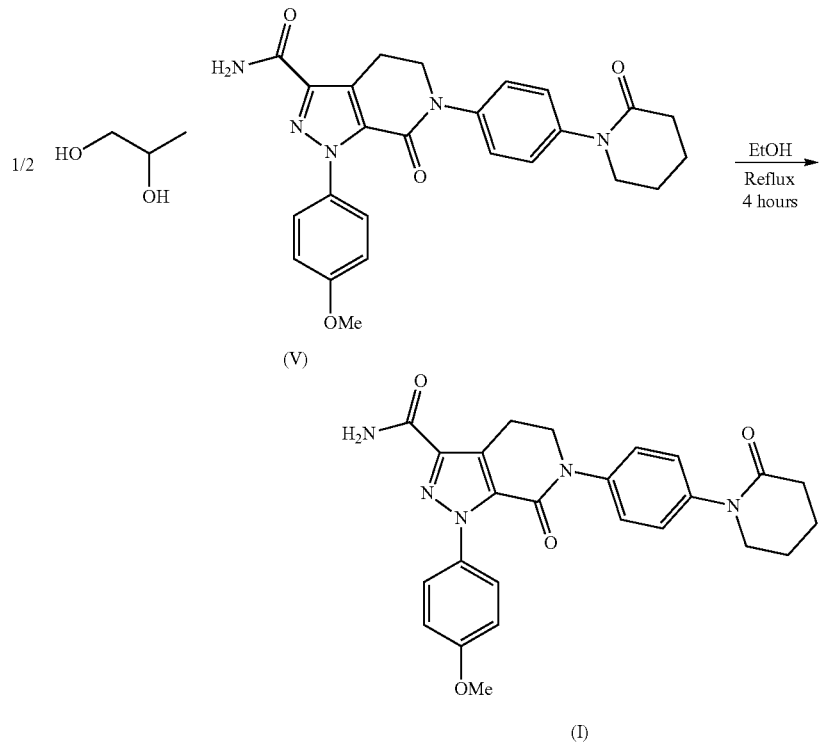

In a round bottom flask were charged Apixaban 1,2-propylene glycol hemisolvate (10 g, 1.0 eq) and ethanol (400 mL) and the mixture was heated to reflux for 4 hours. The suspension was slowly cooled to 20/25° C. and stirred at this temperature for 8 h, then filtered washing with ethanol (2×20 mL). The wet solid was dried under vacuum at 75° C. for 8 h affording 8.1 g of Apixaban N-1 form (0.87 eq). mp 237° C. $^1$H-NMR (400 MHz, DMSO-$d_6$, ppm), δ: 7.74 (s, 1H), 7.53 (d, J=12 Hz, 2H), 7.47 (s, 1H), 7.37 (d, J=8 Hz, 2H), 7.30 (d, J=12 Hz, 2H), 7.02 (d, J=8 Hz, 2H), 4.07 (t, J=8 Hz, 2H), 3.82 (s, 3H), 3.61 (t, J=4 Hz, 2H), 3.23 (t, J=8 Hz, 2H), 2.41 (t, J=4 Hz, 2H), 1.87 (m, 4H). $^{13}$C-NMR and DEPT 135 NMR (100 MHz, DMSO-$d_6$, ppm), δ: 169.3 (C), 163.7 (C), 159.6 (C), 157.1 (C), 142.0 (C), 141.9 (C), 140.3 (C), 133.5 (C), 133.1 (C), 127.3 (C), 126.8 (CH), 126.5 (CH), 125.7 (CH), 113.9 (CH), 56.0 (CH3), 51.3 ($CH_2$), 33.1 ($CH_2$), 23.5 ($CH_2$), 21.5 ($CH_2$), 21.4 ($CH_2$). ESI-MS m/z=460 ([M+H]$^+$).

Example 3

Characterization of Apixaban form N-1.

Apixaban form N-1 obtained by crystallization in EtOH was characterized by several techniques.

FT-IR

FTIR spectrum was recorded using a Thermo Nicolet Nexus 870 FT-IR, equipped with a beamsplitter KBr system, a 35 mW He—Ne laser as the excitation source and a DTGS KBr detector. The spectrum was acquired in 32 scans at a resolution of 4 cm$^{-1}$.

IR (KBr): ν=3483 (m), 3311 (m), 2909 (m), 2866 (W), 1683 (s), 1630 (s), 1595 (s), 1519 (m), 1295 (m), 1256 (m), 975 (m), 848 (s), 813 (m), 668 (m), 467 (m) cm$^{-1}$.

DSC

DSC analysis was recorded with a Mettler DSC822$^e$. A sample of 1.6770 mg was weighed into a 40 μL aluminium crucible with a pinhole lid and was heated, under nitrogen (50 mL/min), at 10° C./min from 30 to 300° C.

Form N-1 is characterized by an endothermic sharp peak corresponding to the melting point with an onset at 235.68° C. (fusion enthalpy −106.66 J/g), measured by DSC analysis (10° C./min).

TGA

Thermogravimetric analysis was recorded in a thermogravimetric analyzer Mettler TGA/SDTA851$^e$. A sample of 4.2206 mg was weighed into a 70 μL alumina crucible with a pinhole lid and was heated at 10° C./min from 30 to 400° C., under nitrogen (50 mL/min). The TG analysis of Form N1 shows a 0.23% weight loss before the melting point (between 130° C. and 230° C.). This loss of weight could come from the elimination of EtOH traces.

X-RPD

XRPD analysis was performed using a PANalytical X'Pert diffractometer with Cu Kα radiation in Bragg-Brentano geometry. The system is equipped with a monodimensional, real time multiple strip detector. The diffractogram was recorded from 3° to 40° (2θ) at a scan rate of 17.6° per minute. List of selected peaks (only peaks with relative intensity greater than or equal to 1% are indicated):

| Pos. [° 2Th.] | Rel. Int. [%] |
|---|---|
| 8.4 | 9 |
| 10.0 | 4 |
| 10.5 | 5 |
| 11.1 | 5 |
| 12.3 | 8 |
| 12.8 | 41 |
| 13.9 | 58 |
| 15.1 | 2 |
| 16.2 | 14 |
| 16.9 | 100 |
| 18.4 | 30 |
| 18.8 | 14 |
| 19.6 | 8 |
| 21.1 | 11 |
| 21.5 | 12 |
| 22.0 | 16 |
| 22.2 | 29 |
| 23.6 | 2 |
| 24.0 | 4 |
| 24.7 | 8 |
| 25.3 | 4 |
| 26.2 | 1 |
| 26.9 | 8 |
| 27.7 | 5 |
| 28.0 | 3 |
| 28.6 | 4 |
| 29.2 | 6 |
| 29.9 | 5 |

-continued

| Pos. [° 2Th.] | Rel. Int. [%] |
|---|---|
| 30.6 | 3 |
| 31.9 | 1 |
| 32.6 | 5 |
| 35.1 | 3 |

In the patent U.S. Pat. No. 7,396,932B2, form N-1 was described by SCXR and $^{13}C$ SSNMR. Using the data of SCXR (unit cell, symmetry and atom positions), XRPD was simulated using the Mercury program. Comparison of this simulated XRPD with the experimental XRPD obtained in example 2 confirmed the formation Apixaban N-1 form.

Karl Fischer

Karl Fischer analyses were recorded with a Metrohm 787 KF Trinito. The product was dissolved in MeOH. Two samples were analyzed using the following reactants: Hydranal-Composite 5 (Riedel de Haën Ref. 34805), Hydranal Methanol Rapid (Riedel de Haën Ref. 37817) and Hydranal Water Standard 1.0 (Riedel de Haën Ref. 34828 used to calculate the factor).

The water content of form N-1 prepared in example 2 is 0.9%.

Example 4

Preparation of Apixaban form N-1 from Apixaban 1,2-Proprylen glycol hemisolvate on larger scale—with seeding of form N-1.

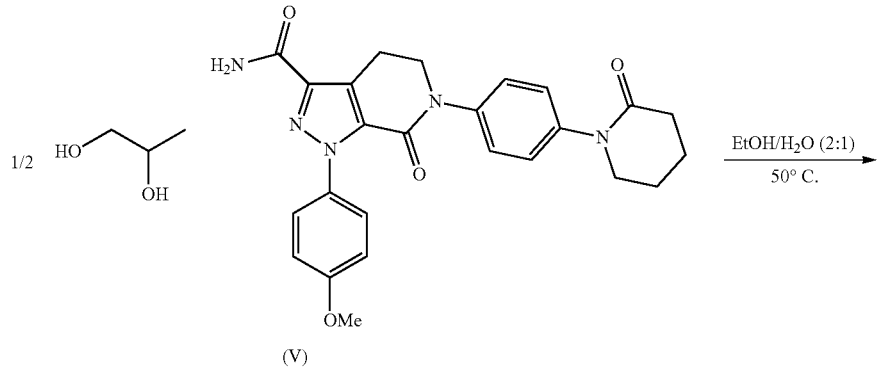

(V)

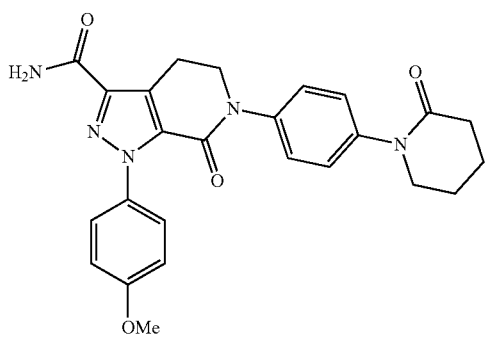

(I)

To a three-necked round-bottomed flask equipped with a thermometer and mechanical stirrer was added Apixaban 1,2-Propylene glycol hemisolvate of formula (V) (85.1 g; 171 mmol), as prepared in Example 1, and a mixture of EtOH/water (2:1) (850 mL, 10 vol.). the resulting suspension was seeded with form N-1 (as prepared in example 2) and it was heated at 50° C. The mixture was maintained at 50° C. for 2.5 hours and then it was cooled down to room temperature. The slurry was stirred at room temperature for 2-3 hours. The solid was filtered with a sintered funnel (porosity 2—very good filtration), washed with EtOH: water (2:1) (170 mL, 2 vol.), with water (170 mL, 2 vol.) and dried under vacuum at 50° C. overnight. Apixaban form N-1 was obtained as off-white powder (65.4 g, 83% yield). $^1$H-NMR analysis shows that the product contains 0.13% of residual Ethanol. K.F. 0.1%. The chemical purity was determinate by HPLC: 99.4%. The starting Apixaban 1,2-Propylene glycol hemisolvate had a purity of 98.3%.

Repeating the above procedure starting from Apixaban 1,2-Propylene glycol hemisolvate with a purity of 95.2%, Apixaban form N-1 was prepared having a purity of 99.5%.

Example 5

Synthesis of the compound of formula (II) in which R is —CH$_2$CH$_2$—.

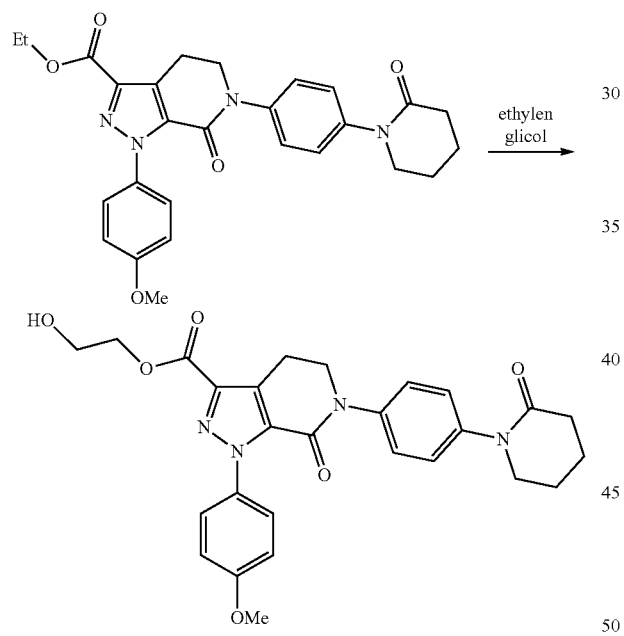

A mixture of Apixaban ethyl ester (10.0 g, 1.0 eq), bibasic potassium phosphate (K$_2$HPO$_4$, 17.8 g, 5.0 eq) and ethylenglycol (1,2-ethan diol, 70 mL) was heated to T=75° C. for 10 h and then cooled to room temperature. Water (70 mL) and dichloromethane (70 mL) were charged and the resulting biphasic solution was stirred at room temperature for 10 min. Once cut the phases, the organic layer was treated with molecular sieves to remove residual water and then concentrated to residue at reduced pressure. The resulting solid was employed without further purification (9.0 g, 0.87 eq). $^1$H-NMR (400 MHz, DMSO-d$_6$, ppm), δ: 7.52 (d, J=12 Hz, 2H), 7.37 (d, J=8 Hz, 2H), 7.30 (d, J=8 Hz, 2H), 7.03 (d, J=12 Hz, 2H), 4.98 (t, J=4 Hz, 1H), 4.35 (t, J=4 Hz, 2H), 4.09 (t, J=4 Hz, 2H), 3.82 (s, 3H), 3.74 (dd, J$_1$=4 Hz, J$_2$=4 Hz, 2H), 3.60 (t, J=4 Hz, 2H), 3.24 (t, J=4 Hz, 2H), 2.40 (t, J=4 Hz, 2H), 1.85 (m, 4H). $^{13}$C-NMR and DEPT 135 NMR (100 MHz, DMSO-d$_6$, ppm), δ: 169.4(C), 162.0(C), 159.8 (C), 156.9(C), 141.9(C), 140.2(C), 139.0(C), 133.5(C), 132.9(C), 127.4 (CH), 127.2(CH), 126.8(CH), 126.5(CH), 114.0(CH), 66.8(CH$_2$), 59.5(CH$_2$), 56.0(CH$_3$), 51.3(CH$_2$), 51.2(CH$_2$), 33.1(CH$_2$), 23.5(CH$_2$), 21.6(CH$_2$), 21.4(CH$_2$). ESI-MS m/z=505 ([M+H]$^+$).

Example 6

Synthesis of the compound of formula (II) in which R is —CH(CH$_3$)$_2$CH$_2$— and —CH$_2$CH(CH$_3$)—.

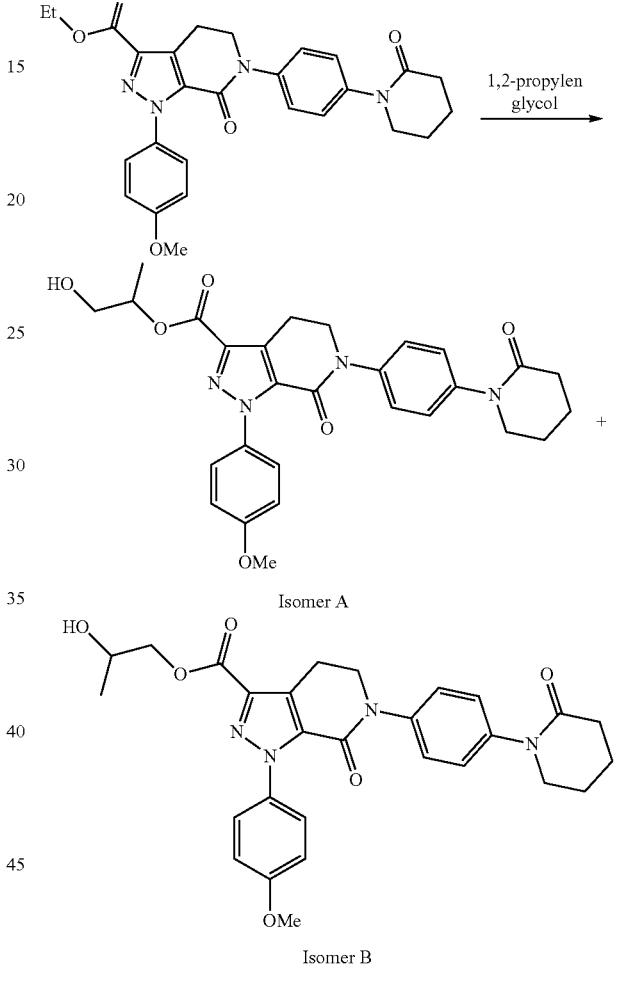

Isomer A

Isomer B

A mixture of Apixaban ethyl ester (30.0 g, 1.0 eq.), bibasic potassium phosphate (K$_2$HPO$_4$, 53.4 g, 5.0 eq.) and propylenglycol (1,2-propan diol, 210 mL) was heated to T=75° C. for 10 h and then cooled to room temperature. Water (210 mL) and dichloromethane (210 mL) were charged and the resulting biphasic solution was stirred at room temperature for 10 min. Once cut the phases, the organic layer was treated with molecular sieves to remove residual water and then concentrated to residue at reduced pressure. The resulting solid is a 1:2 mixture of the two isomers (called isomer A and isomer B respectively in the $^1$H-NMR characterization) was employed without further purification (25.2 g, 0.79 eq). $^1$H-NMR (400 MHz, DMSO-d$_6$, ppm), δ: 7.52 (m, 3H (2H isomer A and 2H isomer B)), 7.37 (m, 3H (2H isomer A and 2H isomer B)), 7.30 (m, 3H (2H isomer A and 2H isomer B)), 7.03 (m, 3H (2H isomer A and 2H isomer B)), 5.12 (m, 0.5H (1H isomer A), 4.96 (m, 1.5H (1H isomer A and 1H isomer B)), 4.20 (m, 2H (2H isomer B)), 4.11 (m, 3H (2H isomer A and 2H isomer B)), 3.98 (m, 1H (1H isomer B)), 3.83 (m, 4.5H (3H isomer A and 3H isomer B)), 3.61 (m, 3H (2H isomer A and 2H isomer B)), 3.26 (m, 3H (2H isomer A and 2H isomer B)), 1.88 (m, 6H (4H isomer A and 4H isomer B)), 1.29 (d, J=4 Hz, 1.5H (3H isomer A)), 1.17 (d, J=4 Hz, 3H (3H isomer B)). $^{13}$C-NMR (100 MHz, DMSO-d$_6$, ppm), δ: 169.4, 161.8, 161.6, 159.8, 156.9, 141.9, 140.2, 139.3, 139.0, 133.5, 133.0, 127.3, 127.2, 126.8, 126.5, 114.0, 72.7, 69.9, 64.5, 64.1, 56.0, 51.3, 51.2, 33.1, 23.5, 21.7, 21.4, 20.5, 16.9 (overlap of some of the two isomers signals was observed). ESI-MS m/z=519 ([M+H]$^+$).

IR (ATR, cm$^{-1}$): 3329, 2934, 2839, 1708, 1673, 1627, 1592, 1511, 1438, 1403, 1372, 1325, 1301, 1252, 1172, 1144, 1054, 1021, 988, 949, 832, 788, 699. X-RPD)(2θ°): 6.7°, 8.2°, 8.5°, 8.9°, 10.5°, 11.1°, 11.6°, 12.1°, 13.0°, 15.3°, 15.9°, 16.8°, 17.2°, 17.9°, 19.3°, 20.1°, 20.4°, 21.3°, 22.8°, 23.2°, 23.8°, 24.5°, 25.4°, 27.9°, 30.3°.

Example 7

Synthesis of the compound of formula (II) in which R is —CH$_2$CH$_2$OCH$_2$CH$_2$—.

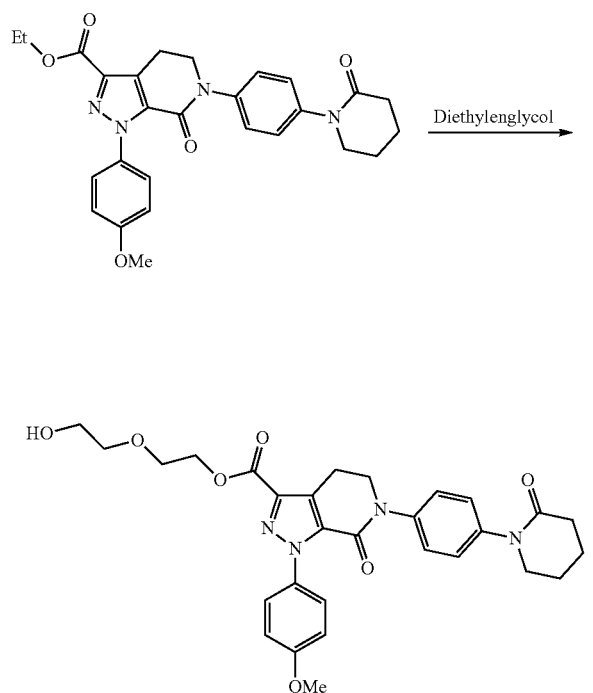

A mixture of Apixaban ethyl ester (10.0 g, 1.0 eq), bibasic potassium phosphate (K$_2$HPO$_4$, 17.8 g, 5.0 eq) and diethylenglycol (70 mL) was heated to T=75° C. for 10 h and then cooled to room temperature. Water (70 mL) and dichloromethane (70 mL) were charged and the resulting biphasic solution was stirred at room temperature for 10 min. Once cut the phases, the organic layer was treated with molecular sieves to remove residual water and then concentrated to residue at reduced pressure. The resulting solid was employed without further purification (10.5 g, 0.93 eq). $^1$H-NMR (400 MHz, DMSO-d$_6$, ppm), δ: 7.53 (d, J=8 Hz, 2H), 7.37 (d, J=8 Hz, 2H), 7.30 (d, J=8 Hz, 2H), 7.03 (d, J=8 Hz, 2H), 4.65 (t, J=4 Hz, 1H), 4.45 (m, 2H), 4.10 (d, J=4 Hz, 2H), 3.83 (s, 3H), 3.77 (m, 2H), 3.53 (m, 4H), 7.53 (d, J=8 Hz, 2H), 3.24 (d, J=8 Hz, 2H), 2.41 (m, 2H), 1.86 (m, 4H). $^{13}$C-NMR and DEPT 135 NMR (100 MHz, DMSO-d$_6$, ppm), δ: 169.4 (C), 161.8 (C), 159.8 (C), 156.9 (C), 141.9 (C), 140.2 (C), 138.8 (C), 133.5 (C), 132.9 (C), 127.5 (C), 127.2 (CH), 126.8 (CH), 126.5 (CH), 114.0 (CH), 72.8 (CH$_2$), 68.7 (CH$_2$), 64.3 (CH$_2$), 60.7 (CH$_2$), 56.0 (CH$_3$), 51.3 (CH$_2$), 51.2 (CH$_2$), 33.1 (CH$_2$), 23.5 (CH$_2$), 21.6 (CH$_2$), 21.4 (CH$_2$). ESI-MS m/z=549 ([M+H]$^+$). KF=0.06%.

Example 8

Synthesis of Apixaban form N-1 from the compound of formula (II) in which R is —CH$_2$CH$_2$—.

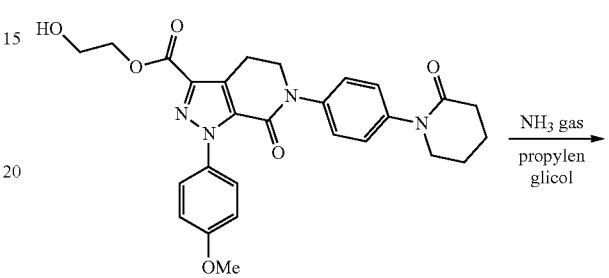

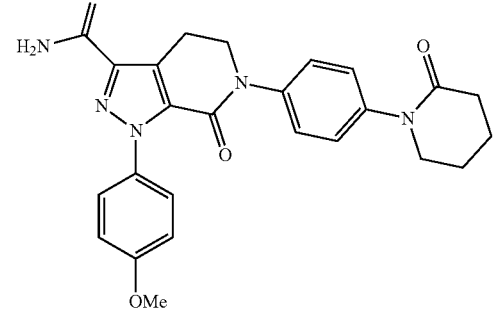

In an autoclave inerted by nitrogen compound of Example 5 (compound of formula (II) in which R is —CH$_2$CH$_2$—, 8.0 g, 1.0 eq) and propylene glycol (1,2-propandiol, 80 mL) were charged and the vessel was pressurized with ammonia at p=4 bar and T=80/85° C. for 6 h. The mixture was then transferred in a round bottom flask, heated to dissolution and diluted with water (16 mL). After stirring at T=95/100° C. for additional 2 h, more water was added (48 mL) and the solution was seeded with Apixaban N-1 form (as prepared in Example 2 or 4). The sus-pension was stirred for 2 h at T=95/100° C., cooled to room temperature and diluted with ethanol (16 mL). After 3 h stirring at T=20/25° C. the slurry was filtered and the wet cake was washed with water (2×8 mL). The solid was dried under vacuum at T=65° C. for 8 h affording Apixaban N-1 form (6.7 g, 0.92 eq). m.p. 237° C. $^1$H-NMR (400 MHz, DMSO-d$_6$, ppm), δ: 7.74 (s, 1H), 7.53 (d, J=12 Hz, 2H), 7.47 (s, 1H), 7.37 (d, J=8 Hz, 2H), 7.30 (d, J=12 Hz, 2H), 7.02 (d, J=8 Hz, 2H), 4.07 (t, J=8 Hz, 2H), 3.82 (s, 3H), 3.61 (t, J=4 Hz, 2H), 3.23 (t, J=8 Hz, 2H), 2.41 (t, J=4 Hz, 2H), 1.87 (m, 4H). $^{13}$C-NMR and DEPT 135 NMR (100 MHz, DMSO-d$_6$, ppm), δ: 169.3 (C), 163.7 (C), 159.6 (C), 157.1 (C), 142.0 (C), 141.9 (C), 140.3 (C), 133.5 (C), 133.1 (C), 127.3 (C), 126.8 (CH), 126.5 (CH), 125.7 (CH), 113.9 (CH), 56.0 (CH$_3$), 51.3 (CH$_2$), 33.1 (CH$_2$), 23.5 (CH$_2$), 21.5 (CH$_2$), 21.4 (CH$_2$). ESI-MS m/z=460 ([M+H]$^+$). KF=0.08%.

Example 9
Synthesis of Apixaban form N-1 from the compound of formula (II) in which R is —CH(CH$_3$)$_2$CH$_2$— and —CH$_2$CH(CH$_3$)—.
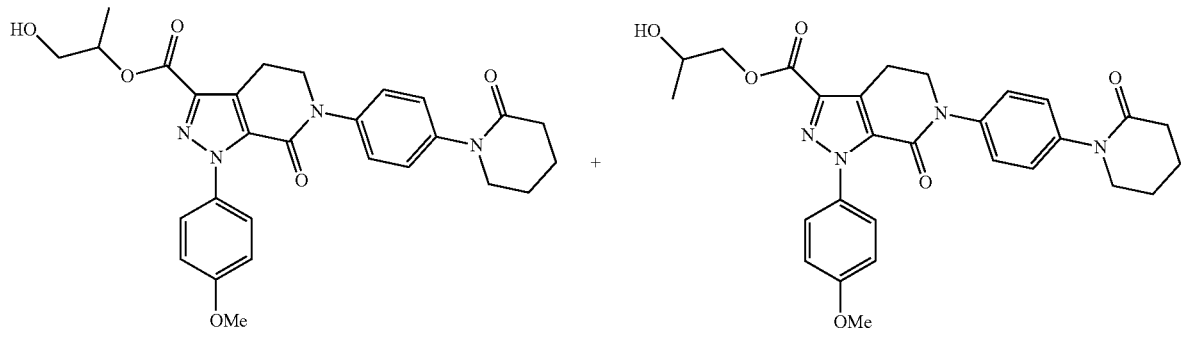
Isomer A + Isomer B
↓ NH$_3$ gas
propylen glicol
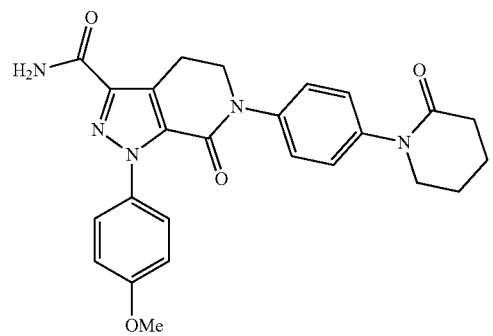

In an autoclave inerted by nitrogen compound of Example 6 (compound of formula (II) in which R is —CH(CH$_3$)$_2$CH$_2$— and —CH$_2$CH(CH$_3$)—, 11 g, 1.0 eq) and propylene glycol (1,2-propandiol, 100 mL) were charged and the vessel was pressurized with ammonia at p=4 bar and T=80/85° C. for 6 h. The mixture was then transferred in a round bottom flask, heated to dissolution and diluted with water (20 mL). After stirring at T=95/100° C. for additional 2 h, more water was added (60 mL) and the solution was seeded with Apixaban N-1 form. The suspension was stirred for 2 h at T=95/100° C., cooled to room temperature and diluted with ethanol (20 mL). After 3 h stirring at T=20/25° C. the slurry was filtered and the wet cake was washed with water (2×10 mL). The solid was dried under vacuum at T=65° C. for 8 h affording Apixaban N-1 form (8.6 g, 0.88 eq). m.p. 237° C. $^1$H-NMR (400 MHz, DMSO-d$_6$, ppm), δ: 7.74 (s, 1H), 7.53 (d, J=12 Hz, 2H), 7.47 (s, 1H), 7.37 (d, J=8 Hz, 2H), 7.30 (d, J=12 Hz, 2H), 7.02 (d, J=8 Hz, 2H), 4.07 (t, J=8 Hz, 2H), 3.82 (s, 3H), 3.61 (t, J=4 Hz, 2H), 3.23 (t, J=8 Hz, 2H), 2.41 (t, J=4 Hz, 2H), 1.87 (m, 4H). $^{13}$C-NMR and DEPT 135 NMR (100 MHz, DMSO-d$_6$, ppm), δ: 169.3 (C), 163.7 (C), 159.6 (C), 157.1 (C), 142.0 (C), 141.9 (C), 140.3 (C), 133.5 (C), 133.1 (C), 127.3 (C), 126.8 (CH), 126.5 (CH), 125.7 (CH), 113.9 (CH), 56.0 (CH$_3$), 51.3 (CH$_2$), 33.1 (CH$_2$), 23.5 (CH$_2$), 21.5 (CH$_2$), 21.4 (CH$_2$). ESI-MS m/z=460 ([M+H]$^+$). KF=0.05%.

Example 10

Synthesis of Apixaban form N-1 from the compound of formula (II) in which R is —CH$_2$CH$_2$OCH$_2$CH$_2$—.

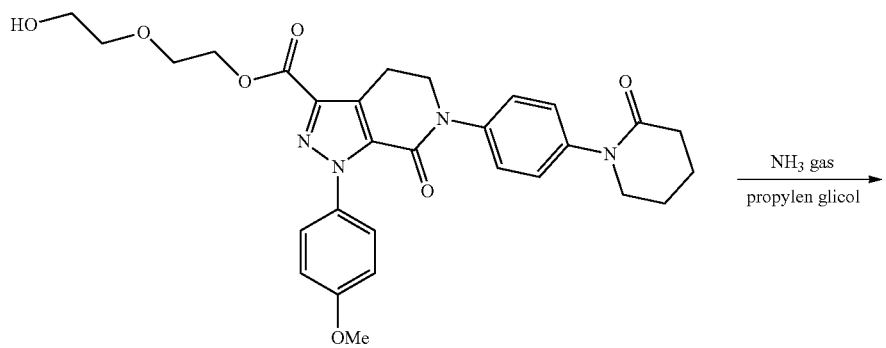

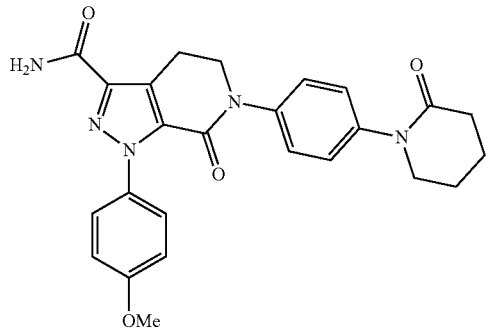

In an autoclave inerted by nitrogen compound of Example 7 (compound of formula (II) in which R is —CH$_2$CH$_2$OCH$_2$CH$_2$—, 9.0 g, 1.0 eq) and propylene glycol (1,2-propandiol, 105 mL) were charged and the vessel was pressurized with ammonia at p=4 bar and T=80/85° C. for 6 h. The mixture was then transferred in a round bottom flask, heated to dissolution and diluted with water (20 mL). After stirring at T=95/100° C. for additional 2 h, more water was added (60 mL) and the solution was seeded with Apixa-ban N-1 form. The suspension was stirred for 2 h at T=95/100° C., cooled to room temperature and diluted with ethanol (20 mL). After 3 h stirring at T=20/25° C. the slurry was filtered and the wet cake was washed with water (2×10 mL). The solid was dried under vacuum at T=65° C. for 8 h affording Apixaban N-1 form (6.5 g, 0.86 eq). mp 237° C. $^1$H-NMR (400 MHz, DMSO-d6, ppm), δ: 7.74 (s, 1H), 7.53 (d, J=12 Hz, 2H), 7.47 (s, 1H), 7.37 (d, J=8 Hz, 2H), 7.30 (d, J=12 Hz, 2H), 7.02 (d, J=8 Hz, 2H), 4.07 (t, J=8 Hz, 2H), 3.82 (s, 3H), 3.61 (t, J=4 Hz, 2H), 3.23 (t, J=8 Hz, 2H), 2.41 (t, J=4 Hz, 2H), 1.87 (m, 4H). $^{13}$C NMR and DEPT 135 NMR (100 MHz, DMSO-d$_6$, ppm), δ: 169.3 (C), 163.7 (C), 159.6 (C), 157.1 (C), 142.0 (C), 141.9 (C), 140.3 (C), 133.5 (C), 133.1

(C), 127.3 (C), 126.8 (CH), 126.5 (CH), 125.7 (CH), 113.9 (CH), 56.0 (CH$_3$), 51.3 (CH$_2$), 33.1 (CH$_2$), 23.5 (CH$_2$), 21.5 (CH$_2$), 21.4 (CH$_2$). ESI-MS m/z=460 ([M+H]$^+$). KF=0.06%.

Example 11

Synthesis of Apixaban form N-1—from the compound of formula (III) in which R is —CH$_2$CH$_3$ (Example 6 of WO2007/0001385)—Comparative example

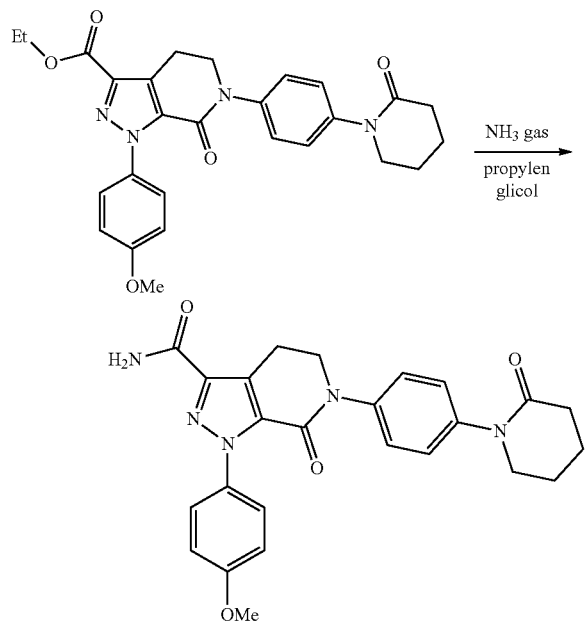

In an autoclave inerted by nitrogen Apixaban ethyl ester (65 g, 1.0 eq) and propylene glycol (1,2-propan diol, 455 mL) were charged and the vessel was pressurized with ammonia at p=4 bar and T=80/85° C. for 6 h. The mixture was then transferred in a round bottom flask washing the autoclave with propylene glycol (65 mL), heated to dissolution and diluted with water (130 mL). After stirring at T=95/100° C. for additional 2 h, more water was added (390 mL) and the solution was seeded with Apixaban N-1 form. The suspension was stirred for 2 h at T=95/100° C., cooled to room temperature and diluted with ethanol (130 mL). After 3 h stirring at T=20/25° C. the slurry was filtered and the wet cake was washed with water (2×130 mL). The solid was dried under vacuum at T=65° C. for 8 h affording Apixaban N-1 form (56.0 g, 0.917 eq). m.p. 237° C. $^1$H-NMR (400 MHz, DMSO-d$_6$, ppm), δ: 7.74 (s, 1H), 7.53 (d, J=12 Hz, 2H), 7.47 (s, 1H), 7.37 (d, J=8 Hz, 2H), 7.30 (d, J=12 Hz, 2H), 7.02 (d, J=8 Hz, 2H), 4.07 (t, J=8 Hz, 2H), 3.82 (s, 3H), 3.61 (t, J=4 Hz, 2H), 3.23 (t, J=8 Hz, 2H), 2.41 (t, J=4 Hz, 2H), 1.87 (m, 4H). $^{13}$C-NMR and DEPT 135 NMR (100 MHz, DMSO-d$_6$, ppm), δ: 169.3 (C), 163.7 (C), 159.6 (C), 157.1 (C), 142.0 (C), 141.9 (C), 140.3 (C), 133.5 (C), 133.1 (C), 127.3 (C), 126.8 (CH), 126.5 (CH), 125.7 (CH), 113.9 (CH), 56.0 (CH$_3$), 51.3 (CH$_2$), 33.1 (CH$_2$), 23.5 (CH$_2$), 21.5 (CH$_2$), 21.4 (CH$_2$). ESI-MS m/z=460 ([M+H]$^+$). KF=0.08%.

Example 12

Reaction rate of the synthesis of Apixaban from the compound of formula (II) compared with the synthesis of Apixaban from Apixaban ethyl ester. An effect of the invention.

Apixaban can be obtained from compound of formula (II) (as described in Example 9, Example 10 or Example 11) or, according to prior art method, from Apixaban ethyl ester (as described in comparative Example 11), (see also example 6 of WO2007/0001385). However, the reaction rate is considerably faster when starting from a compound of formula (II), for example, the compound (II) in which R is —CH$_2$CH(CH$_3$)— and CH(CH$_3$)$_2$CH$_2$— (called Propylen glycol ester in FIG. 1 and Table 1).

As depicted in FIG. 1, reaction completion (conversion >99%) is reached within 3 h employing the Propylen glycol ester as starting material (triangles in FIG. 1) while it takes at least 6 h, under exactly the same reaction conditions, from the Apixaban ethyl ester to reach the same conversion value (circles in FIG. 1).

Moreover, comparing the data collected after 6 hours, the amount of Apixaban is higher when it is prepared from the Propylene glycol ester (99.25% versus 98.95%).

The detailed data are collected in Table 1 for the kinetic study of the conversion of Propylen glycol ester to Apixaban and for the conversion of Apixaban ethyl ester to Apixaban.

TABLE 1

| Comparative kinetic study | | | | |
|---|---|---|---|---|
| | Propylene glycol ester-> Apixaban | | Apixaban glycol ester-> Apixaban | |
| Time (h) | Propylen glycol ester | Apixaban | Apixaban ethyl ester | Apixaban |
| 0.0 | 100.0% | 0.00% | 100.0% | 0.00% |
| 1.0 | 9.46% | 90.54% | 20.86% | 61.79% |
| 2.0 | 1.54% | 98.55% | — | — |
| 3.0 | 0.83% | 99.17% | — | — |
| 3.5 | — | — | 0.64% | 98.25% |
| 6.0 | 0.75% | 99.25% | 0.28% | 98.95% |

Data are expressed as HPLC conversions.

Example 13

HPLC method for the identification and quantification of the compound of formula (II) in which R is —CH(CH$_3$)$_2$CH$_2$— (Isomer A) and —CH$_2$CH(CH$_3$)— (Isomer B) which are typical process intermediates and impurities.

As mentioned in Example 10, compound of formula (II), in particular the compound of formula (II) in which R is —CH$_2$CH(CH$_3$)— and —CH(CH$_3$)CH$_2$—, is also a typical impurity found in the isolated Apixaban product obtained by the process of the invention described in the Examples above.

This species could be identified and monitored via the following HPLC method:

| Chromatographic conditions: | |
|---|---|
| Column: | XBridge C18 150 × 4.6 mm 3.5 μm |
| Temp. Column: | 40° C. |
| Mobile Phase A: | H$_2$O MilliQ/Methanol 90/10 |
| Mobile Phase B: | Acetonitrile/Methanol 90/10 |
| Gradient: | Time (min) | % A | % B |
| | 0 | 83.5 | 16.5 |
| | 20 | 5.5 | 94.5 |
| | 25 | 5.5 | 94.5 |
| Post run: | 7 min. |
| Flow: | 1.0 mL/min |

-continued

| Chromatographic conditions: | |
|---|---|
| Detector | UV a 252 nm |
| Injection Volume: | 5 μL |
| Run Time: | 25 min |
| Sample diluent: | $CH_2Cl_2/EtOH/H_2O$ 1:5:4 |

Applying the conditions described above the expected retention times are as indicated below:

| Compound | RRT |
|---|---|
| Apixaban | 1.00 |
| Propylen glycol ester—Isomer B | 1.16 |
| Propylen glycol ester—Isomer A | 1.18 |
| Apixaban ethyl ester | 1.467 |

The amount of the compound of formula (II) into Apixaban is determined in percent area.

The invention claimed is:

1. A compound of formula (II):

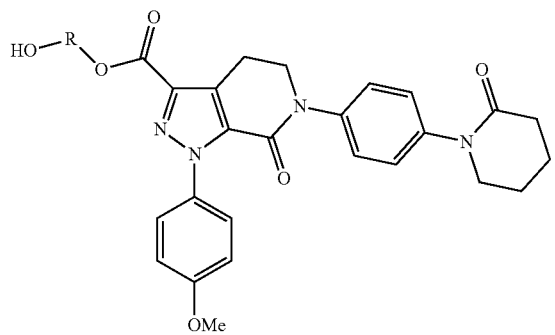

(II)

wherein R is selected from the group consisting of a linear or branched $C_2-C_6$ alkyl, —$CH_2CH(OH)$—$CH_2$— and —$(R^1O)_nR^1$— wherein $R^1$ is a linear or branched $C_2-C_4$ alkyl an n is an integer from 1 to 6.

2. The compound of formula (II) according to claim 1, wherein R is selected from the group consisting of —$CH_2CH_2$—, —$CH_2CH(CH_3)$—, —$CH(CH_3)CH_2$—, —$(CH_2)_3$— and —$CH_2CH_2OCH_2CH_2$—.

3. A process for the preparation of a compound of formula (II) according to claim 1, by means of a transesterification reaction of the compound of formula (III):

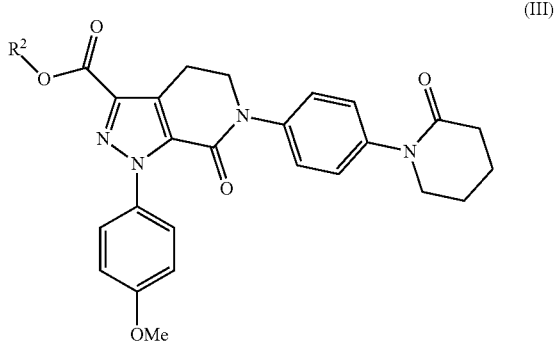

(III)

wherein $R^2$ is a linear or branched $C_2-C_6$ alkyl.

* * * * *